US010197499B2

(12) United States Patent
King

(10) Patent No.: US 10,197,499 B2
(45) Date of Patent: Feb. 5, 2019

(54) WAVEGUIDE SENSOR WITH NANOPOROUS SURFACE LAYER

(71) Applicant: Corning Incorporated, Corning, NY (US)

(72) Inventor: Jeffrey Stapleton King, Menlo Park, CA (US)

(73) Assignee: Corning Incorporated, Corning, NY (US)

( * ) Notice: Subject to any disclaimer, the term of this patent is extended or adjusted under 35 U.S.C. 154(b) by 250 days.

(21) Appl. No.: 15/093,163

(22) Filed: Apr. 7, 2016

(65) Prior Publication Data

US 2017/0292914 A1    Oct. 12, 2017

(51) Int. Cl.
G01N 21/64 (2006.01)
G01N 21/77 (2006.01)
G01N 21/65 (2006.01)

(52) U.S. Cl.
CPC ....... *G01N 21/645* (2013.01); *G01N 21/6428* (2013.01); *G01N 21/7703* (2013.01); *G01N 21/658* (2013.01); *G01N 2021/6432* (2013.01); *G01N 2021/6465* (2013.01); *G01N 2021/6482* (2013.01); *G01N 2021/7726* (2013.01); *G01N 2021/7786* (2013.01)

(58) Field of Classification Search
CPC combination set(s) only.
See application file for complete search history.

(56) References Cited

U.S. PATENT DOCUMENTS

| | | | |
|---|---|---|---|
| 5,082,629 A | 1/1992 | Burgess, Jr. et al. | |
| 5,250,095 A | 10/1993 | Sigel, Jr. et al. | |
| 5,272,518 A | 12/1993 | Vincent | |
| 5,446,534 A | 8/1995 | Goldman | |
| 7,355,162 B2 | 4/2008 | Sidorin | |
| 7,864,321 B2 | 1/2011 | Caron et al. | |
| 7,889,336 B2 | 2/2011 | Yankov | |

(Continued)

FOREIGN PATENT DOCUMENTS

| | | |
|---|---|---|
| CA | 2590813 C | 9/2013 |
| JP | 2009085714 A | 4/2009 |

(Continued)

OTHER PUBLICATIONS

Delaizir et al. "Infrared glass-ceramics with fine porous surfaces for optical sensor applications" Journal of the American Ceramic Society 90(7) pp. 2073-2077, 2007.

(Continued)

*Primary Examiner* — Brian R Gordon

(74) *Attorney, Agent, or Firm* — Russell S. Magaziner

(57) ABSTRACT

A waveguide sensor system is provided. The system includes a light source and a waveguide formed from a light transmitting material. Light from the light source enters the waveguide at an input area and travels within the waveguide by total internal reflection to an analyte area and light to be analyzed travels within the waveguide from the analyte area by total internal reflection to an output area. An optical sensor is coupled to the output area and is configured to interact with the light to be analyzed. The system includes a plurality of pores located along the outer surface within the analyte area and formed in the light transmitting material of the waveguide, and the pores are configured to enhance light interaction with the analyte within the analyte area.

10 Claims, 4 Drawing Sheets

(56) References Cited

U.S. PATENT DOCUMENTS

| | | | |
|---|---|---|---|
| 8,642,319 | B2 | 2/2014 | Kasai et al. |
| 8,837,871 | B2 | 9/2014 | Fujii et al. |
| 9,075,017 | B2 | 7/2015 | Kasai et al. |
| 2002/0191884 | A1 | 12/2002 | Letant et al. |
| 2003/0133639 | A1 | 7/2003 | Tao et al. |
| 2009/0034902 | A1 | 2/2009 | Izmailov |
| 2010/0067015 | A1 | 3/2010 | Matsushita et al. |
| 2010/0098592 | A1 | 4/2010 | Rong et al. |
| 2012/0213669 | A1 | 8/2012 | Kasai et al. |
| 2013/0114077 | A1 | 5/2013 | Zhang |
| 2014/0105789 | A1 | 4/2014 | Kasai et al. |
| 2014/0152914 | A1 | 6/2014 | King |
| 2016/0265974 | A1 | 9/2016 | Ertel et al. |
| 2017/0212043 | A1 | 7/2017 | Daly et al. |

FOREIGN PATENT DOCUMENTS

| | | |
|---|---|---|
| JP | 2010117204 A | 5/2010 |
| JP | 2010203838 A | 9/2010 |
| JP | 05792489 B2 | 10/2015 |
| WO | 2013102661 A1 | 7/2013 |

OTHER PUBLICATIONS

International Search Report and Written Opinion PCT/US2017/025855 dated Jul. 10, 2017.

Hotta et al.; "Nanoporous Waveguide Sensor with Optimized Nanoarchitectures for Highly Sensitive Label-Free Biosensing"; ACSNano, vol. 6, No. 2 (2012); pp. 1541-1547.

Lau et al.; "Highly Sensitive Detection of Processes Occurring Inside Nanoporous Anodic Alumina Templates: A Waveguide Optical Study"; J. Phys. Chem. B 2004, 108; pp. 10812-10818.

Ning et al.; "Nano-porous polymer films for optical planar waveguide"; Proceedings of SPIE vol. 4904 (2002); pp. 490-494.

Qi et al.; "Nanoporous leaky waveguide based chemical and biological sensors with broadband spectroscopy"; Applied Physics Letters 90, (2007); pp. 011102-011102-3.

Fu et al.; "Surface-enhanced Raman scattering (SERS) biosensing based on nanoporous dielectric waveguide resonance"; Sensors and Actuators B 201 (2014); pp. 173-176.

Fan et al.; "Enhanced fluorescence in a nanoporous waveguide and its quantitative analysis"; Optics Express, vol. 20, No. 12 (Jun. 4, 2012); pp. 12850-12859.

Chaganti et al; "A Simple Minature Optical Spectrometer With a Planar Waveguide Grating Coupler in Combination with a Plano-Convex Lens"; Optics Express; vol. 14, No. 9; May 1, 2006, pp. 4064-4072.

Chen et al; "The Application of Linear Variable Filter to Improve the Resolution of Micro Spectrometer Systems"; Advanced Materials Research vols. 443-444 (2012), pp. 159-159.

Emadi et al; "An UV Linear Variable Optical Filter-Based Micro-Spectrometer"; Procedia Engineering 5 (2010) 416-419.

Emadi et al; "Design, Fabrication and Measurements With a UV Linear-Variable Optical Filter Microspectrometer"; Proc. of SPIE, vol. 8439, 84390V-1-84390V-10.

Goldman et al; "Minaturized Spectrometer Employing Planar Waveguides and Grating Couplers for Chemical Analysis"; Applied Optics, Nov. 1, 1990, vol. 29, No. 31 pp. 4583-4589.

Grabarnik et al; "Planar Double-Grating Microspectrometer"; Optics Express, vol. 15, No. 6, Mar. 19, 2007, 3581-3588.

Obrien et al; "Minature Near-Infrared (NRS) Spectrometer Engine for Handheld Applications"; Proc. of SPIE, vol. 8374, pp. 837404-1-837404-8.

Pederson et al; "Pocket-Size Near-Infrared Spectrometer for Narcotic Material Identification"; Proc. of SPIE, vol. 9101; pp. 91010O-1-91010O-11.

Sander et al; "Selffocussing Phase Transmission Grating for an Integrated Optical Microspectrometer"; Sensors and Actuators A, 88 (2001) 1-9.

Stookey et al; Full-Color Photosensitive Glass, 49 J. Applied Physics 5114 (1978); pp. 5114-5123.

Xu et al; "Performance Analysis of a Portable Imaging Spectrometer Using Linear Variable Optical Filter"; Proceedings SPIE, Vol. 4922 (2002) pp. 188-194.

Zhang et al; "Minature Spectrometer Based on Linear Variable Interference Filters"; SPIE, vol. 3855 pp. 42-50.

ns having a wavelength and a
waveguide formed from a light transmitting material. The
WAVEGUIDE SENSOR WITH NANOPOROUS SURFACE LAYER

BACKGROUND

The disclosure relates generally to the field of sensors, and specifically to a sensor utilizing a waveguide having a porous surface within an analyte interaction region. Generally, the amount or type of a chemical or analyte can be detected by measuring a property of light, such as intensity or wavelength, that has interacted with or has been emitted from an analyte or related detection chemicals. The measured property of the light is then correlated to a property of the analyte (e.g., type of material, amount or concentration of a particular material, etc.) such that the property of the analyte may be measured.

SUMMARY

One embodiment of the disclosure relates to a waveguide optical sensing system, The system comprises a light source configured to generate light having a wavelength and a waveguide formed from a light transmitting material. The waveguide having an input area, an output area, an outer surface and analyte area located along the outer surface. The light from the light source enters the waveguide at the input area and travels within the waveguide by total internal reflection to the analyte area and light to be analyzed travels within the waveguide from the analyte area by total internal reflection to the output area. The system includes an optical sensor coupled to the output area, and the optical sensor is configured to interact with the light to be analyzed and configured to generate a signal related to a property of light to be analyzed. The system includes a plurality of pores located along the outer surface within the analyte area and formed in the light transmitting material of the waveguide. The pores have an average pore width, wherein the average pore width is less than 30% of the wavelength.

An additional embodiment of the disclosure relates to a glass sensor system including a sheet of glass material including a first major surface and a porous area located along the first major surface. The system includes a light source directing light into a first region of the sheet of glass material such that the light travels within the sheet of glass material by total internal reflection to the porous area where the light interacts with an analyte. The system includes a light sensitive device coupled to a second region of the sheet of glass material, and the light sensitive device interacts with light traveling from the porous area by total internal reflection to the second region. The light sensitive device is configured to generate a signal related to a property of the light interacting with the light sensitive device. The porous area includes a plurality of pores formed in the glass material, and the pores have an average pore width of less than 100 nm.

An additional embodiment of the disclosure relates to a sensor waveguide configured for use as part of a sensing system. The sensor waveguide includes a sheet of light transmitting material that includes a first major surface, a second major surface opposite the first major surface and an analyte contact area located on the first major surface. The sensor waveguide includes a plurality of pores formed in the light transmitting material within the analyte contact area, wherein the pores have an average pore width of less than 100 nm. The sensor waveguide includes a layer of an analyte responsive material supported by the first major surface within the analyte contact area, and at least some of the analyte responsive material is located within the plurality of pores.

Additional features and advantages will be set forth in the detailed description that follows, and, in part, will be readily apparent to those skilled in the art from the description or recognized by practicing the embodiments as described in the written description and claims hereof, as well as the appended drawings.

It is to be understood that both the foregoing general description and the following detailed description are merely exemplary, and are intended to provide an overview or framework to understand the nature and character of the claims.

The accompanying drawings are included to provide a further understanding and are incorporated in and constitute a part of this specification. The drawings illustrate one or more embodiment(s), and together with the description serve to explain principles and the operation of the various embodiments.

DETAILED DESCRIPTION

Figure 1:
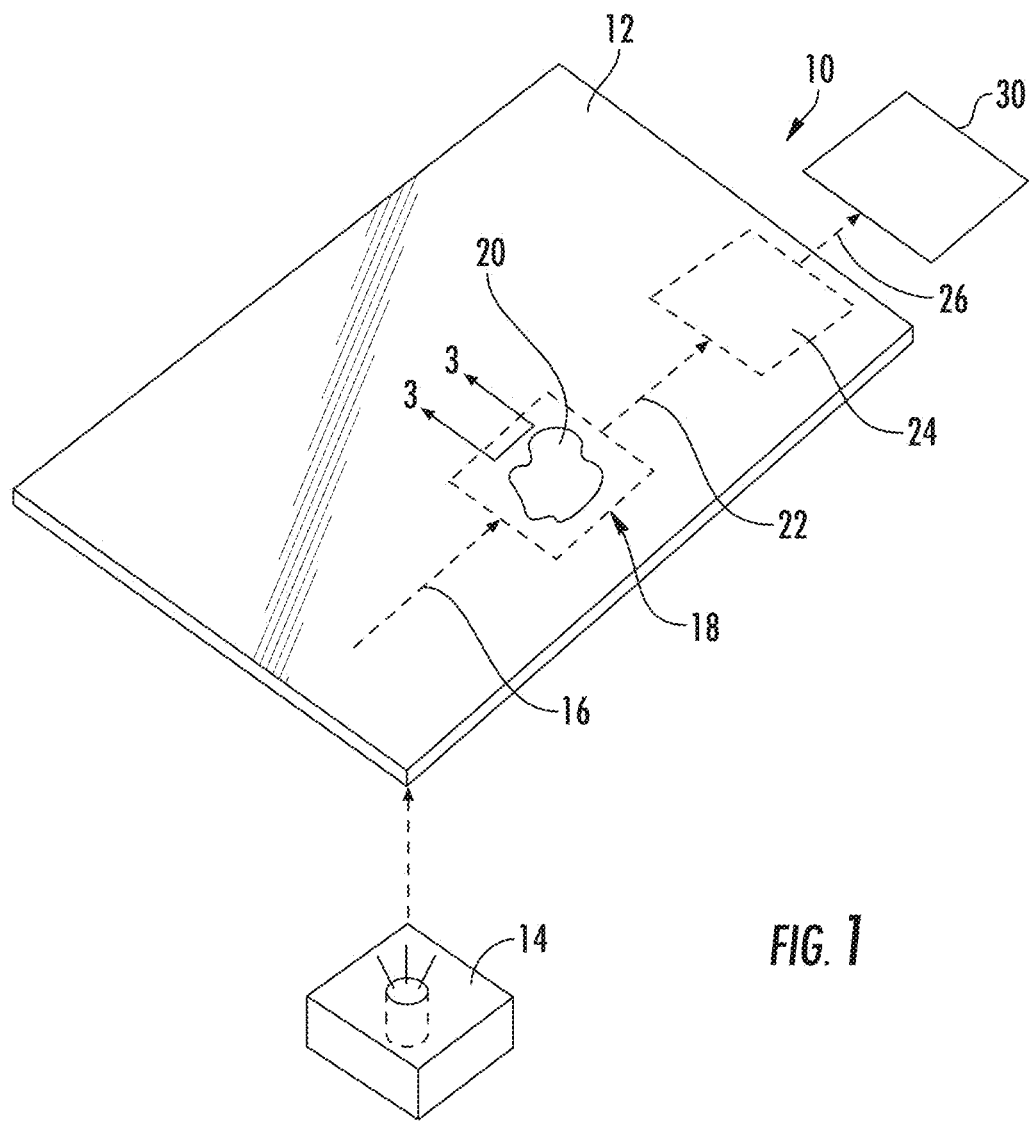
FIG. 1 shows an exploded view of a glass waveguide sensor according to an exemplary embodiment.

Referring generally to the figures, various embodiments of a sensing system that utilize a waveguide as part of its optics system are shown. In general, the sensing system includes a light source (e.g., an LED) that launches light into the waveguide, the light travels within the waveguide via total internal reflection to an analyte area located on at least one surface of the waveguide. The light interacts with the analyte, for example, directly or indirectly through an analyte responsive material, generating light to be analyzed. Light to be analyzed travels via total internal reflection from the analyte area to an optical sensor (e.g., CCD, photodiode, etc.), which generates a signal related to a property (e.g., intensity, wavelength, etc.) of light to be analyzed.

In the embodiments discussed herein, the waveguide includes a plurality of pores (e.g., nanopores) located along the surface of the waveguide within the analyte area. In various embodiments discussed herein, the pores are sized (e.g., depth, width, diameter, etc.) or shaped to facilitate/improve function of the waveguide based sensor. For example, it is believed that the pores increase the surface area within the analyte area, which in turn increases the area available for the light within the waveguide to interact with the analyte or with the analyte responsive material. Further, in embodiments that utilize an analyte responsive material coated to the outer surface of the waveguide, the pores increase the surface area available for supporting the analyte reactive material as well as the portion of the analyte material exposed to interaction with the analyte (at least compared to a surface without pores). It is believed that the increased surface area and light interaction provided by the porous surface discussed herein increases the sensitivity of the waveguide sensor discussed herein.

While the pores are sized to be large enough to provide the surface area and light interaction benefits discussed above, the pores discussed herein are sized to be small enough to allow the light transmitting component to function as a waveguide. In various embodiments, the pores are sized relative to the wavelength of the light from light source such that the light is allowed to efficiently propagate within the light transmitting material via total internal reflection. In various embodiments, the light transmitting material may be glass, ceramic, plastics, etc. that allow for light conduction via total internal reflection. For example, in various embodiments, pores are sized such that the diameter and/or depth of the pores are less than the wavelength of the light from the light source and/or are less than the wavelength of the light to be analyzed. Applicant has found that by sizing pores as discussed herein to be smaller than the wavelength of the light within glass waveguide, the amount of scattering and/or outcoupling of light along the surface of the waveguide can be reduced/eliminated allowing the glass to function efficiently as waveguide. Thus, Applicant has developed a design for a porous surface waveguide that strikes a balance between providing pores that allow the glass to function efficiently as a waveguide while at that same time providing the surface area and light interaction benefits discussed above.

Further, in various embodiments, the pores of the waveguide based sensor system discussed herein are formed directly into the glass material at the surface of the waveguide, rather than including a separate porous outer layer (e.g., anodic alumina) applied onto a surface of the glass of the waveguide. Thus, the waveguide based sensor system discussed herein provides a monolithic waveguide arrangement in which light within the waveguide is permitted to interact directly with the analyte or the analyte responsive material without traversing into or interacting through a separate outer porous coating layer. In at least some embodiments, it is believed that this monolithic arrangement provides for improved light to analyte interaction which in turn improves sensor performance while at the same time providing a robust and thermally stable structure that eliminates issues that may be present with a coating layer. Further, the monolithic arrangement discussed herein eliminates the processing complexity typically associated with depositing an additional coating layer on the glass.

Referring to FIG. 1, a waveguide optical sensing system, for example a waveguide based glass sensor system 10, is shown according to an exemplary embodiment. Sensor system 10 includes a waveguide formed from a light transmitting material, shown as glass sheet 12. In other embodiments, the light transmitting material may be any suitable waveguide material, including ceramic, plastics, etc. that allow for light conduction via total internal reflection. As described in more detail below, glass sheet 12 acts as a pathway to direct and contain light traveling between the various components of sensor system 10.

Sensor system 10 includes a light source 14 that directs light, shown graphically as the arrow labeled 16, into glass sheet 12. In various embodiments, light source 14 may be a broad spectrum light source, such as a white light LED, and in other embodiments, light source 14 may be a narrow spectrum light source generating a particular spectrum of light to be used for a particular application, such as a blue light LED. As will be understood, in some embodiments, the wavelength(s) of light generated by light source 14 are selected based on suitability for detection/interaction with a desired analyte and/or for interaction with a particular analyte responsive material. In FIG. 1 light source 14 is shown spaced from glass sheet 12 to better show the components of sensor system 10, but in an exemplary embodiment, light source 14 closely abuts or contacts glass sheet 12 to increase the portion of light generated by light source 14 that is received into glass sheet 12. In some embodiments, light source 14 is bonded to (or otherwise in intimate contact with) glass sheet 12 such that light from light source 14 is coupled into the glass sheet, and in such embodiments, a light coupling structure (e.g., a prism coupler, a scattering material, etc.) is not utilized to couple light into the glass. However, in some other embodiments, glass sheet 12 may include one or more light coupling structure (e.g., a prism coupler, a scattering material, etc.) which facilitates coupling of light from light source 14 into glass sheet 12.

In the embodiment shown, sensor system 10 includes an analyte area 18 that can support or otherwise come into contact with a material to be analyzed, shown as analyte 20. In general, light 16 travels within glass sheet 12 via total internal reflection from light source 14 to analyte area 18 where light 16 interacts with analyte 20 (either directly or indirectly) resulting in the yield, production, generation or alternation of light to be analyzed, shown graphically by the arrow labeled 22. In at least some embodiments, by utilizing glass sheet 12 as a waveguide, the interaction between the light with the system and the analyte is increased by the multiple reflections that occur as the light travels within the waveguide. As shown in the embodiment of FIG. 1, analyte area 18 occupies a portion, less than the entire area of the upper surface of glass sheet 12.

In general, light to be analyzed 22 travels via total internal reflection within glass sheet 12 to an optical detector or sensor, shown as photodiode 24. As will be understood, photodiode 24 is a device which interacts with light to be analyzed 22 and generates a signal 26 (e.g., an electronic signal) related to a property of light to be analyzed 22 (e.g., intensity, wavelength, etc.). It should be understood that in various embodiments, the light sensitive device of sensor system 10 may include any suitable light sensitive device, including charge coupled devices (CCDs), photodiodes, photodiode arrays, photoconductors, phototransistors, photomultiplier tubes, etc.

Signals 26 are received and processed by a processing circuit, such as processor 30. In general, processor 30 is configured with hardware and/or software for receiving signals 26 and for processing signals 26 to determine one or more characteristic (e.g., presences, amount, concentration, type, etc.) of analyte 20. In various embodiments, processor 30 can include a wide range of hardware and/or software that receives and processes signals 26. For example, in some embodiments, data acquisition and processing includes DC measurement of the resulting photocurrent from photodiode 24 when light source 14 is turned on. In other embodiments, data acquisition and processing includes various modulated approaches that are capable of phase shift measurements or low signal measurements with interference (e.g. ambient light) rejection. In various embodiments, processor 30 may be a processor of a portable general purpose computing device, such as a smartphone, tablet, smartwatch, smartglasses, laptop, etc. In other embodiments, processor 30 may be the dedicated processor (e.g., a dedicated processor, microprocessor, ASIC, etc.) of a dedicated sensor system.

In general, sensor system 10 may be a wide variety of sensing systems configured to measure, detect or monitor a wide variety of analytes. For example, sensor system 10 may be configured to measure, detect or monitor various gases, chemicals, liquids, biomarkers, etc. In addition, in some embodiments, sensor system 10 may include multiple analyte areas 18 each configured to detect or measure a different analyte and/or different properties of the same analyte. In some such embodiments, each of the different analyte areas 18 may include different analyte responsive materials for interacting with the desired analyte. In other embodiments, system 10 may be configured for other light analysis applications, such as spectrophotometer applications.

Figure 2:
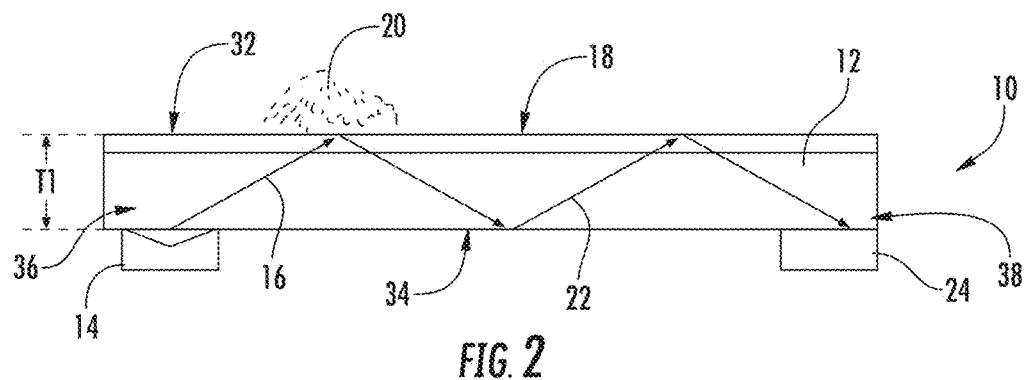
FIG. 2 is a schematic side view of the glass waveguide sensor of FIG. 1 according to another exemplary embodiment.

Referring to FIG. 2, a side view of a sensor system 10 is shown according to an exemplary embodiment. Glass sheet 12 includes a first major surface, shown as upper surface 32, and a second major surface, shown as lower surface 34. As shown schematically in FIG. 2, light 16 and light 22 travels via total internal reflection within the thickness of glass sheet 12. In this arrangement, analyte area 18 is located on or is formed in upper surface 32, and both light source 14 and photodiode 24 are located along or are supported from lower surface 34. In the embodiment shown, light source 14 is in contact with lower surface 34 such that light 16 is allowed to efficiently enter glass sheet 12, and photodiode 24 is located along lower surface 34 such that light is able to exit glass sheet 12 to interact with photodiode 24. Further, in this arrangement, analyte area 18 is located between light source 14 and photodiode 24, and specifically light source 14 and photodiode 24 are located along opposite edges of glass sheet 12.

As noted above, glass sheet 12 acts as an optical waveguide such that light is carried between the different components of sensor system 10 via total internal reflection. Accordingly, in this arrangement glass sheet 12 has an input area 36 at which light source 14 is located and an output area 38 at which photodiode 24 is located. Thus, in this arrangement, glass sheet 12 acts as a waveguide carrying light 16 within glass sheet 12 from input area 36 to analyte area 18. At analyte area 18, light 16 within glass sheet 12 interacts, either directly or indirectly, with analyte 20 on upper surface 32 (e.g., via evanescent light interaction, via optical coupling due to index matching, critical angle change when analyte 20 is a liquid, absorption, photoluminescence, etc.) yielding light to be analyzed 22. Glass sheet 12 also acts as a waveguide directing light to be analyzed 22 toward output area 38 where the light 22 interacts with photodiode 24.

In some embodiments, glass sheet 12 as a whole acts as the waveguide. In some other embodiments, glass sheet 12 as a whole may not act as the waveguide but may include waveguide sections or embedded waveguides. For example, the glass waveguides discussed herein may be laser written waveguide sections within glass sheet 12 and/or ion-exchange waveguides embedded within glass sheet 12.

Further, in some embodiments as shown in FIG. 2, the analyte area 18 occupies the entire area of surface 32, and in other embodiments, analyte area 18 occupies less than all of the area of surface 32. Glass sheet 12 includes a thickness, T1, between upper surface 32 and lower surface 34. In particular embodiments, T1 is between 20 micrometers and 4 millimeters, and specifically is between 20 micrometers and 2 millimeters. In the embodiments shown, surface 32 (except for the pores discussed herein) and surface 34 are substantially planar, parallel surfaces, and in other embodiments, surface 32 and/or surface 34 may be a convex or concave curved surfaces, may be angled relative to each other or may include other complex curves or shapes.

Figure 3:
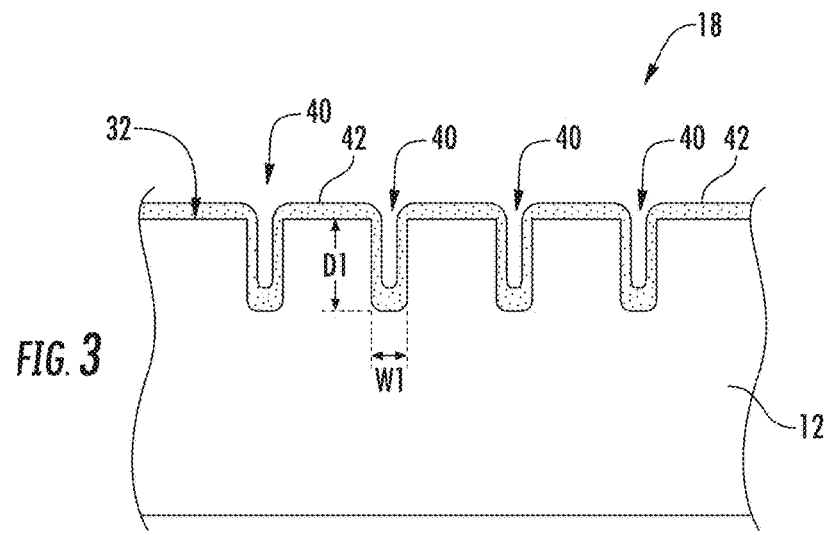
FIG. 3 is a detailed cross-sectional view of an analyte area of a glass waveguide sensor according to an exemplary embodiment.
Figure 4:
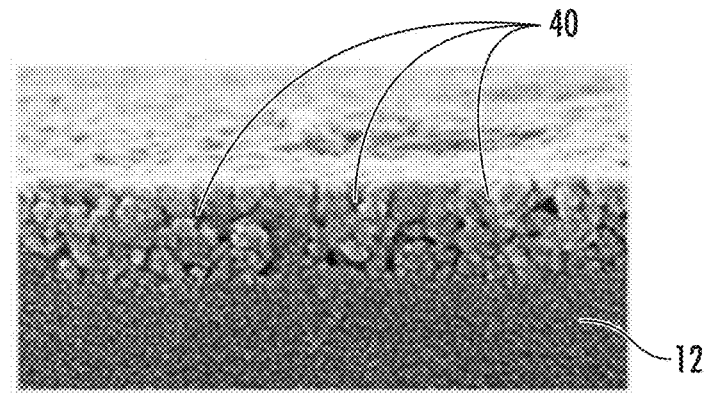
FIG. 4 is a micrograph image of a porous surface of a glass waveguide sensor according to an exemplary embodiment.

Referring to FIG. 3, a schematic cross-sectional view of analyte area 18 is shown. Glass sheet 12 includes a plurality of pores 40 formed in the glass material of sheet 12 and located along outer surfaces 32 within analyte area 18. As shown in FIG. 3, pores 40 may be wells, recesses, channels, depressions, etc. formed along outer surface 32 of glass sheet 12. In general, pores 40 are sized and/or positioned along surface 32 in a manner that increases or improves the ability of light traveling within glass sheet 12 to interact with an analyte while at the same time allowing glass sheet 12 to function as a waveguide. It should also be understood, that while the schematic view of FIG. 3 shows pores 40 as a substantially consistent well-like structure for ease of depiction, pores 40 may be an interconnected sponge-like three dimensional, network of pores located adjacent one or more surface of glass sheet 12, as shown in FIG. 4. In particular, pores 40 are believed to increase the area of surface 32 (as compared to a nonporous, planar surface) which provides the interaction interface between the light within glass sheet 12 and the analyte, and it is believed that by increasing the area of this interaction interface, sensor system 10 provides a more sensitive and/or more accurate ability to sense an analyte within analyte area 18. Further, in contrast to some materials that utilize a porous coating applied to a glass or ceramic material (e.g., a porous anodic alumina coating), pores 40 provide the increased light/analyte interaction area in a monolithic structure without the need for a separate additional layer. Applicant also believes that the monolithic construction and pore arrangement discussed herein provides for a thermally stable sensor system, lends itself to thin device applications and/or lends itself for use with multiplexed detecting materials.

In various embodiments, pores 40 are specifically sized large enough to provide this increased light/analyte interaction area, while at the same time sized relative to the wavelength of light 16 from light source 14 and/or to the wavelength of light to be analyzed 22 to limit or prevent scattering or outcoupling that may otherwise occur along a porous waveguide surface. In various embodiments, pores 40 have an average pore width, shown representatively as W1, and an average pore depth, shown representatively as D1. In general, average pore width W1 is average of the dimension perpendicular to the thickness of glass sheet 12 for the pores 40 of analyte area 18, and in embodiments where pores 40 are substantially circular in cross-section, W1 represents an average diameter. In general, average pore depth D1 is the average of the pore dimension parallel to the thickness of glass sheet 12 for the pores 40 of analyte area 18.

In various embodiments, W1 is less than 30% of the wavelength of light 16 and/or of the wavelength of light 22, specifically less than 10% of the wavelength of light 16 and/or of the wavelength of light 22, and more specifically is between 1% and 9% of the wavelength of light 16 and/or of the wavelength of light 22. In some such embodiments, W1 may also be greater than 0.1% and more specifically greater than 1% of the wavelength of light 16 and/or of the wavelength of light 22. In specific embodiments, W1 is greater than 4% and less than 6% of the wavelength of light 16 and/or of the wavelength of light 22, and specifically, W1 is about 5% (e.g., 5% plus or minus 10%) of the wavelength of light 16 and/or of the wavelength of light 22. In various embodiments, W1 is less than 100 nm, and more specifically is greater than 1 nm and less than 30 nm.

In various embodiments, D1 is less than the wavelength of light 16 and/or is less than the wavelength of the wavelength of light 22, specifically less than 50% of the wavelength of light 16 and/or of the wavelength of light 22, and more specifically less than 30% of the wavelength of light 16 and/or of the wavelength of light 22. In some such embodiments, D1 may also be greater than 5% and more specifically 10% of the wavelength of light 16 and/or of the wavelength of light 22. In various embodiments, D1 is between 10 nm and 10 μm.

In various embodiments, pores 40 increase the surface area of surface 32 as compared to a planar nonporous surface. In various embodiments, the area of surface 32 is 200% greater, 300% greater, or 500% greater than a nonporous planar glass surface having the same outer dimensions as analyte area 18. In specific embodiments, the area of surface 32 is between 400% and 1000% greater than a nonporous planar glass surface having the same outer dimensions as analyte area 18. In a particular embodiment, the percentage of free space or air within the porous zone of glass sheet 12 can be more than 30%, more than 50% and more than 75%, and in such embodiments the degree of porosity can be defined in terms of the percentage of free space in the network.

In some embodiments, sensor system 10 may be configured to allow light 16 to interact directly with an analyte at surface 32, and in some such embodiments, light within glass sheet 12 interacts with the analyte via evanescent light interaction, via optical coupling due to index matching, via critical angle change or via absorption.

In other embodiments, sensor system 10 includes a layer of analyte responsive material supported by surface 32 and located at least in part within pores 40. In general, analyte responsive material is any material that interacts with light 16 and/or analyte 20 such that light to be analyzed 22 is related to or varies based on a property of analyte 20 (e.g., presences/absence, amount, concentration, etc. of analyte 20). In such embodiments, by coating pores 40 with the analyte responsive material the portion of the analyte responsive material available to interact with light 16 at the interface between the glass and the analyte responsive material is increased. Similarly, by coating pores 40 with the analyte responsive material the portion of the analyte responsive material available to interact with analyte 20 at the interface between the analyte and the analyte responsive material is increased.

As shown in FIG. 3, the analyte responsive material may be a fluorescent analyte responsive material, shown as a layer of analyte sensitive fluorophore material 42. In this embodiment, analyte sensitive fluorophore material 42 is applied in a layer, coating surface 32 and located within pores 40 within analyte area 18. In a particular embodiment, analyte sensitive fluorophore material 42 is a material that is excited by light 16 causing fluorescence and in which an intensity or other characteristic of the fluorescence generated by analyte sensitive fluorophore material 42 varies in the presence of the analyte. In this manner, light to be analyzed 22 includes the fluorescent light from analyte sensitive fluorophore material 42 and the intensity or other property of the fluorescent light is related to the presence or amount of the analyte located at analyte area 18.

In a particular embodiment, analyte sensitive fluorophore material 42 is an $O_2$ sensitive fluorophore, and in a specific embodiment, analyte sensitive fluorophore material 42 is an Ru-complex, such as tris(4,7-diphenyl-1, 10-phenanthroline) ruthenium(II) dichloride. In such embodiments utilizing this analyte reactive material, analyte 20 is oxygen, and fluorescence of the analyte sensitive fluorophore material 42 is reduced (e.g., via quenching) in the presence of oxygen and the degree of fluorescence reduction is related to the amount of oxygen present at analyte area 18. Thus, in such embodiments, the intensity of the fluorescent component of light to be analyzed 22 is related to the amount of oxygen present to interact with analyte sensitive fluorophore material 42. In this arrangement, the signal 26 generated by photodiode 24 is related to the amount of atmospheric oxygen present at analyte area 18, which can be read and processed by processor 30.

It should be understood, that while FIGS. 1-3, show a sensor system in which analyte area 18 is an outer or upper surface of glass sheet 12, other glass waveguide sensor arrangements are contemplated utilizing the nanoporous surface arrangements discussed herein. For example, in one embodiment, sensor system 10 includes a porous analyte area 18 in the center of a glass waveguide arrangement formed by pressing two glass sheets coated with an analyte responsive material together with sufficient flatness to maintain waveguided modes in both glass layers. In other embodiments, glass sheet 12 may be a multilayer (e.g., a two or three layer) fusion formed glass sheet, and in a specific embodiment, one or more of the glass layers of the multilayer glass sheet is a layer of leached Vycor glass available from Corning, Inc.

In addition to pores 40, the surface within analyte area 18 may be further modified to enhance interaction of light with analyte 20. In an exemplary embodiment, sensor system 10 includes silver nanoparticles embedded in surface 32 within analyte area 18 which is believed to enhance interaction between light 16 and analyte 20 via surface enhanced Raman scattering (SERS). In such embodiments, the silver nanoparticles may be embedded in the glass in situ or may be deposited onto surface 32 after formation of pores 40.

Referring to FIG. 4, a micrograph image of pores 40 within a glass sheet 12 is shown according to an exemplary embodiment. As shown in the image of FIG. 4 and as noted above, pores 40 form a three-dimensional network of pores adjacent one of the surfaces of glass sheet 12. In the embodiment shown in FIG. 4, pores 40 are formed via a chemical etching processes. However, in other embodiments, pores 40 may be formed through any suitable process including, laser etching, photolithography, e-beam lithography, self-assembly of an etch mask, nanoimprint lithography, phase separation (e.g., detirification of Vycor glass) combined with selective etching, use of block copolymer masks, etc. In such embodiments, glass sheet 12 may be fabricated via a technique which results in glass with porous surfaces and in such embodiments, pores 40 are not formed via a secondary formation step.

Figure 5:
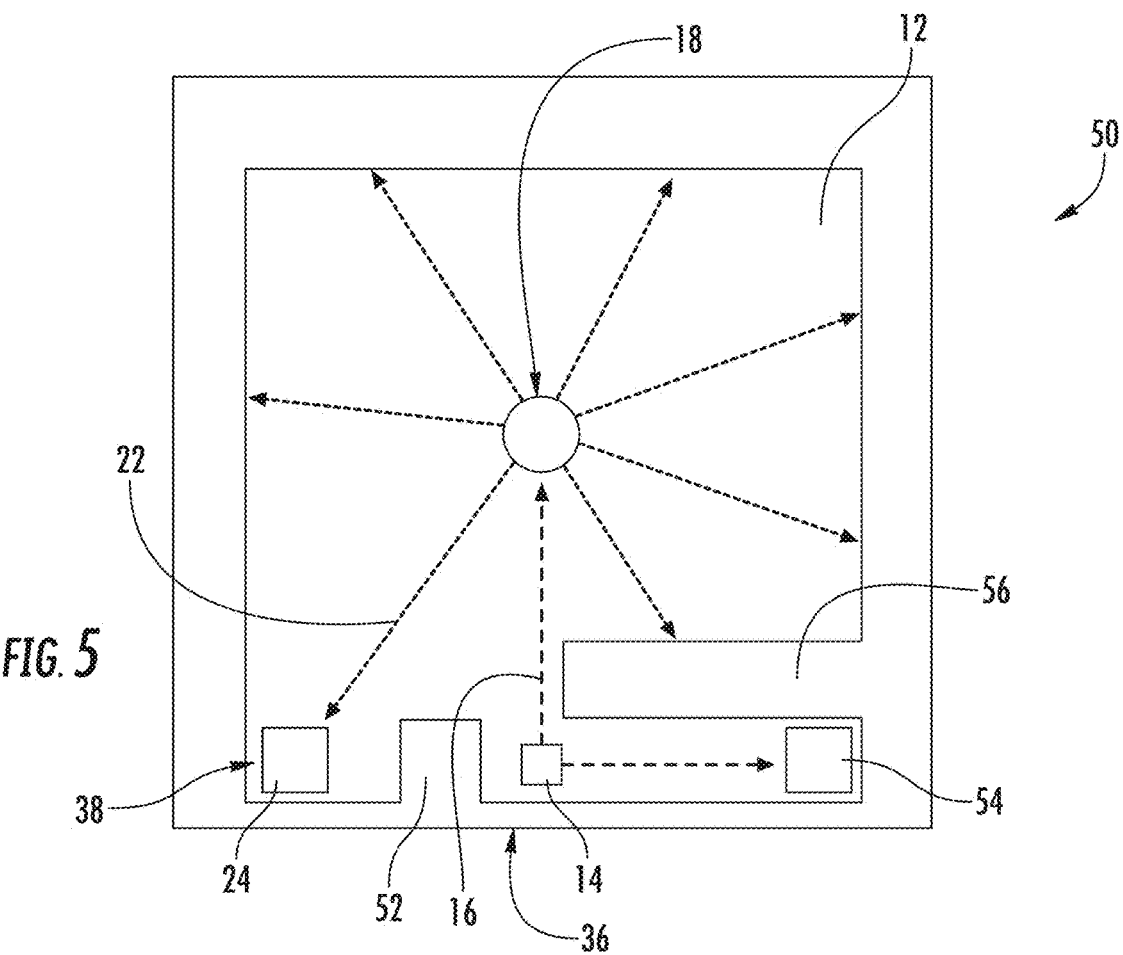
FIG. 5 is a top plan view of a glass waveguide sensor according to another exemplary embodiment.

Referring to FIG. 5, a waveguide optical sensing system, such as waveguide based glass sensor system 50, is shown according to an exemplary embodiment. Sensor system 50 is substantially the same as sensor system 10 except as discussed herein. Similar to sensor system 10, sensor system 50 includes an analyte area 18 that receives light 16, and light to be analyzed 22 leaves analyte area 18 to interact with photodiode 24. However, in the arrangement shown in FIG. 5, light source 14 and photodiode 24 are generally located on the same side of analyte area 18, and in particular are located adjacent to a common edge of glass sheet 12. In this arrangement, system 50 includes a light blocking structure 52 located between light source 14 and photodiode 24 such that light 16 is blocked from traveling directly from light source 14 to photodiode 24. This arrangement limits or prevents photodiode 24 from being saturated by direct light 16 allowing photodiode 24 to be responsive to or increase responsiveness to light to be analyzed 22.

Further, sensor system 50 also includes a second optical sensor, shown as second photodiode 54. In general, photodiode 54 is configured to receive light 16 from light source 14 and to generate a signal related to a property of light 16, and this signal is communicated to processor 30. Thus, in this arrangement, photodiode 54 monitors the output of light source 14 and allows operation of system 50 to be adjusted or controlled in real time in relation to the measured light output from light source 14. For example, a measured level of fluorescence from a fluorescent analyte responsive material may be related to both a characteristic (e.g., intensity, wavelength, etc.) of light 16 and to the amount of analyte present. Thus, by monitor operation of light source 14 via photodiode 54, system 50 can more accurately measure the desired property of the analyte by adjusting readings based on fluctuations in the output of light source 14.

Sensor system 50 also includes a second light blocking structure 56 located between analyte area 18 and second photodiode 54 such that light to be analyzed 22 traveling away from analyte area 18 is blocked from directly traveling to second photodiode 54. This arrangement limits or prevents photodiode 54 from experiencing cross-talk with the light to be analyzed 22, which allows photodiode 54 to be responsive to or increases responsiveness to light 16. In general, light blocking structures 52 and 56 may be any suitable structure for limiting or preventing light from reaching photodiodes 24 and 54, respectively. In various embodiments, light blocking structures 52 and 56 may be opaque physical structures, reflective structures, light absorbing structures, optical filters, etc.

In various embodiments, glass sheet 12 may be formed from a wide variety of suitable glass materials capable of functioning as a waveguide. In various embodiments, glass sheet 12 may be formed from a fusion drawn glass material, and in specific embodiments, glass sheet 12 may be EagleXG glass, Gorilla Glass, high purity fused silica (HPFS), Vycor glass or Iris Glass available from Corning, Inc. In various embodiments, glass sheet 12 may be formed in a wide range of sizes as desired for certain applications. In various embodiments, the width and/or length of glass sheet 12 may be between 5 millimeters and 250 centimeters. In some embodiments, a subsection of glass sheet 12 may be utilized as the waveguide for sensor system 10, and in other embodiments, the entirety of glass sheet 12 may be used as the waveguide for sensor system 10. In various embodiments, glass sheet 12 may configured to provide sensing in a number of different application. For example, glass sheet 12 may substrate in a dedicated sensor device, cover glass equipped with a sensor for mobile electric device, cover glass equipped with a sensor for display device, automotive glass, building/architectural glass, etc.

Figure 6A:
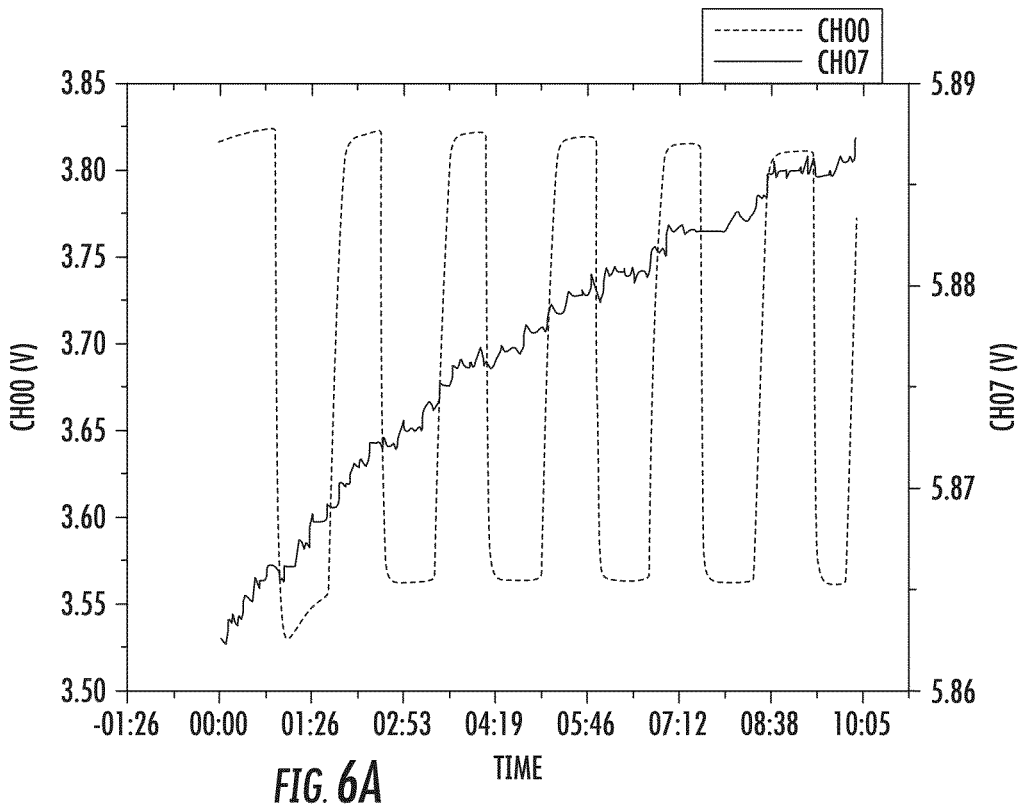
FIGS. 6A and 6B are graphs showing degree of quenching in the presence of differing levels of oxygen detected using a glass waveguide sensor according to an exemplary embodiment.
Figure 6B:
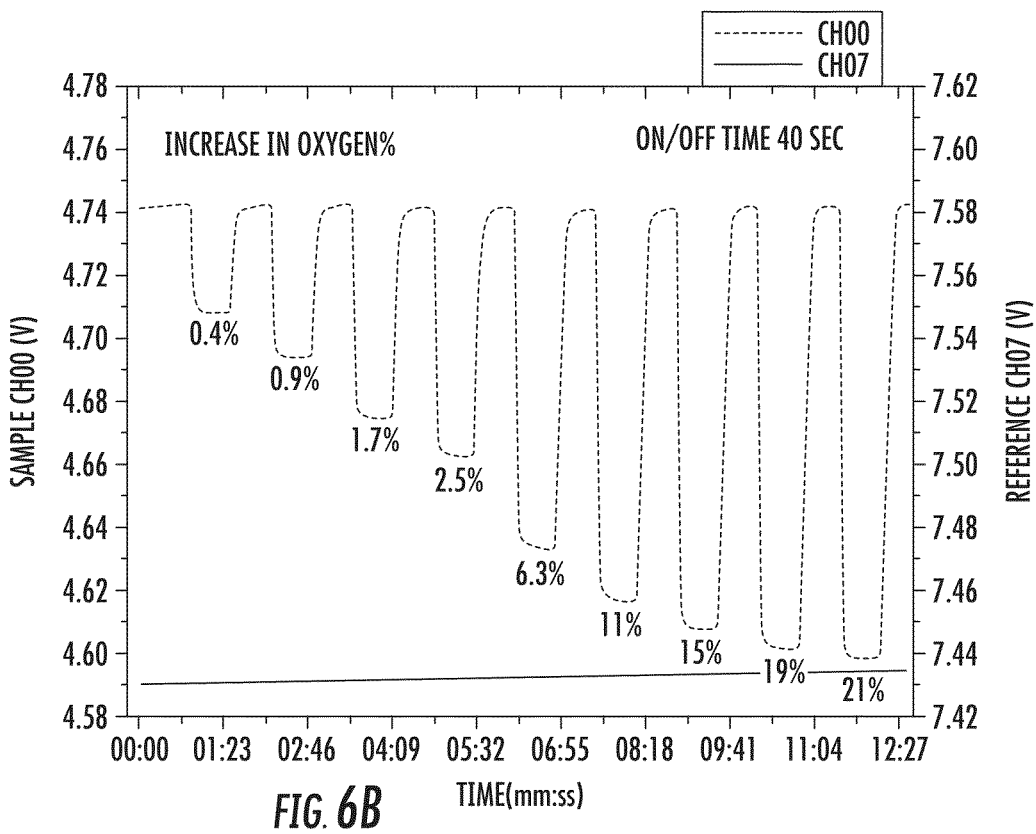

FIGS. 6A and 6B show data generated from operating systems such as discussed herein demonstrating that a repeatable signal proportional to $O_2$ concentration can be generated utilizing a glass sheet waveguide including a nanoporous analyte area supporting an Ru-complex, specifically tris(4,7-diphenyl-1,10-phenanthroline) ruthenium(II) dichloride, as an analyte sensitive fluorophore material, as discussed above. In one embodiment, CH00 is the output from photodiode 24, and CH07 is the output from photodiode 54 as shown in FIG. 5. The hardware used to acquire the data in FIGS. 6A and 6B included a waveform generator, an LED/laser driver, and a lock-in amplifier. Oxygen content was varied using mass flow controllers. The data in FIGS. 6A and 6B shows clear quenching of the Ru-complex fluorescence with increasing oxygen.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that any particular order be inferred. In addition, as used herein, the article "a" is intended to include one or more component or element, and is not intended to be construed as meaning only one.

It will be apparent to those skilled in the art that various modifications and variations can be made without departing from the spirit or scope of the disclosed embodiments. Since modifications, combinations, sub-combinations and variations of the disclosed embodiments incorporating the spirit and substance of the embodiments may occur to persons skilled in the art, the disclosed embodiments should be construed to include everything within the scope of the appended claims and their equivalents.

What is claimed is:

1. A waveguide optical sensing system comprising:
    a light source configured to generate light, to be analyzed, having a wavelength:
    a light transmitting material,
    a waveguide formed from the light transmitting material, the waveguide having an input area, an output area, an outer surface and analyte area located along the outer surface, wherein generated light from the light source enters the waveguide at the input area and travels within the waveguide by total internal reflection to the analyte area and the generated light to be analyzed travels within the waveguide from the analyte area by total internal reflection to the output area;
    an optical sensor coupled to the output area, the optical sensor configured to interact with the generated light to be analyzed and configured to generate a signal related to a property of the generated light to be analyzed;
    pores located along the outer surface within the analyte area and formed in the light transmitting material, wherein the pores have an average pore width, wherein the average pore width is less than 30% of the wavelength: and
    a first light blocking structure located between the light source and the optical sensor such that generated light is blocked from traveling directly from the light source to the optical sensor.

2. The waveguide optical sensing system of claim 1, further comprising:
    a second optical sensor configured to receive light from the light source and to generate a signal related to a property of the light generated by the light source; and
    a second light blocking structure located between the analyte area and the second optical sensor such that the light to be analyzed traveling away from the analyte area is blocked from directly traveling from the analyte area to the second optical sensor.

3. The waveguide optical sensing system of claim 1, wherein the light transmitting material is a monolithic sheet of glass.

4. The waveguide optical sensing system of claim 1, wherein light within the waveguide directly interacts with analyte or analyte responsive material without traversing into or interacting through a separate outer porous coating layer.

5. A waveguide optical sensing system, comprising:

a light source configured to generate light, to be analyzed, having a wavelength;

a light transmitting material wherein the light transmitting material is a sheet of glass having a first major surface, a second major surface opposing the first major surface and a thickness between the first major surface and second major surface, a waveguide formed from the light transmitting material the waveguide having an input area, an output area, an outer surface and analyte area located along the outer surface, wherein generated light from the light source enters the waveguide at the input area and travels within the waveguide by total internal reflection to the analyte area and the generated light to be analyzed travels within the waveguide from the analyte area by total internal reflection to the output area;

an optical sensor coupled to the output area, the optical sensor configured to interact with the generated light to be analyzed and configured to generate a signal related to a property of the generated light to be analyzed;

pores located along the outer surface within the analyte area and formed in the light transmitting material, wherein the pores have an average pore width, wherein the average pore width is less than 30% of the wavelength: and wherein the outer surface of the waveguide is at least one of the first major surface and the second major surface.

6. The waveguide optical sensing system of claim 5, wherein the analyte area and the pores are formed on the first major surface, and the input area and the output area are located along the second major surface.

7. The waveguide optical sensing system of claim 6, wherein the sheet of glass has a thickness between 20 μm and 4 mm.

8. The waveguide optical sensing system of claim 5, wherein light within the waveguide directly interacts with analyte or analyte responsive material without traversing into or interacting through a separate outer porous coating layer.

9. The waveguide optical sensing system of claim 5, further comprising a first light blocking structure located between the light source and the optical sensor such that light is blocked from traveling directly from the light source to the optical sensor.

10. The waveguide optical sensing system of claim 9, further comprising:

a second optical sensor configured to receive light from the light source and to generate a signal related to a property of the light generated by the light source; and a second light blocking structure located between the analyte area and the second optical sensor such that the light to be analyzed traveling away from the analyte area is blocked from directly traveling from the analyte area to the second optical sensor.

* * * * *

UNITED STATES PATENT AND TRADEMARK OFFICE
CERTIFICATE OF CORRECTION

PATENT NO. : 10,197,499 B2
APPLICATION NO. : 15/093163
DATED : February 5, 2019
INVENTOR(S) : Jeffrey Stapleton King Page 1 of 1

It is certified that error appears in the above-identified patent and that said Letters Patent is hereby corrected as shown below:

On the Title Page

On page 2, Column 2, item (56), other publications, Line 7, delete "Minature" and insert -- Miniature --, therefor.

On page 2, Column 2, item (56), other publications, Line 12, delete "Adavanced" and insert -- Advanced --, therefor.

On page 2, Column 2, item (56), other publications, Line 19, delete ""Minaturized" and insert -- "Miniaturized --, therefor.

On page 2, Column 2, item (56), other publications, Line 24, delete ""Minature" and insert -- "Miniature --, therefor.

On page 2, Column 2, item (56), other publications, Line 38, delete ""Minature" and insert -- "Miniature --, therefor.

Signed and Sealed this
Tenth Day of December, 2019

Andrei Iancu
*Director of the United States Patent and Trademark Office*